US012142160B1

(12) United States Patent
Helali et al.

(10) Patent No.: US 12,142,160 B1
(45) Date of Patent: Nov. 12, 2024

(54) CATEGORIZATION OF STUDENTS WITH INTELLECTUAL LEARNING DIFFICULTIES THROUGH ANALYSIS OF BRAIN ACTIVITY ENERGY EMISSION

(71) Applicant: KING FAISAL UNIVERSITY, Al-Ahsa (SA)

(72) Inventors: Mamdouh Mosaad Ahmed Helali, Al-Ahsa (SA); Rommel Mahmoud Ali Alali, Al-Ahsa (SA); Mohammed Saeed Alarji Alqahtani, Al-Ahsa (SA); Amani Mohammed Bukhamseen, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/434,142

(22) Filed: Feb. 6, 2024

(51) Int. Cl.
*A61B 5/372* (2021.01)
*A61B 5/384* (2021.01)
*G09B 5/02* (2006.01)

(52) U.S. Cl.
CPC ............... *G09B 5/02* (2013.01); *A61B 5/372* (2021.01); *A61B 5/384* (2021.01)

(58) Field of Classification Search
CPC ......... A61B 5/0006; A61B 5/16; A61B 5/165; A61B 5/168; A61B 5/291; A61B 5/31; A61B 5/316; A61B 5/369; A61B 5/372; A61B 5/384
See application file for complete search history.

(56) References Cited

U.S. PATENT DOCUMENTS

| 9,230,321 B2 | 1/2016 | El-Baz et al. |
| 10,068,490 B2 | 9/2018 | Hibbs et al. |
| 11,311,220 B1* | 4/2022 | Al-Saggaf ............... A61B 5/165 |
| 2004/0077967 A1* | 4/2004 | Jordan ................... A61B 5/316 |
| | | 600/544 |

(Continued)

FOREIGN PATENT DOCUMENTS

WO     2020226257 A1     11/2020

OTHER PUBLICATIONS

Ning-Han Liu et al.; "Recognizing the Degree of Human Attention Using EEG Signals from Mobile Sensors"; Sensors 2013, 13, 10273-10286; doi: 10.3390/s130810273, Sensors (Basel). Aug. 2013; 13(8): 10273-10286. Published online Aug. 9, 2013. doi: 10.3390/s130810273.

(Continued)

*Primary Examiner* — Chu Chuan Liu
(74) *Attorney, Agent, or Firm* — Nath, Goldberg & Meyer; Joshua B. Goldberg

(57) ABSTRACT

An electronic device that detects and analyzes the energy emitted by brains of individuals. This device measures and analyzes the energy emitted from the brain activity of, for example, students, enabling the classification of students with learning difficulties based on the quantity of emitted energy. Leveraging established measuring devices, supported by computer programs akin to those utilized in electrocardiography, enables the prediction of both the quantity and speed of brain energy based on the magnetic field's intensity. By comparing the intensity of the magnetic field resulting from electrochemical energy in the brain with standard measurements for the general populace, learning difficulties can be diagnosed effectively.

10 Claims, 1 Drawing Sheet

(56) References Cited

U.S. PATENT DOCUMENTS

2006/0257834 A1  11/2006  Lee et al.
2011/0144519 A1   6/2011  Causevic
2015/0141287 A1   5/2015  Mncent

OTHER PUBLICATIONS

Agatha Lenartowicz, Ph. D et al.; "Use of EEG to Diagnose ADHD"; Curr Psychiatry Rep. Author manuscript; available in PMC Nov. 4, 2015. Published in final edited form as: Curr Psychiatry Rep. Nov. 2014; 16(11): 498. doi: 10.1007/s11920-014-0498-0.

Kaido Värbu, et al.; "Past, Present, and Future of EEG-Based BCI Applications"; Sensors (Basel). May 2022; 22(9): 3331. Published online Apr. 26, 2022. doi: 10.3390/s22093331 Sensors 2022, 22, 3331.

* cited by examiner

CATEGORIZATION OF STUDENTS WITH INTELLECTUAL LEARNING DIFFICULTIES THROUGH ANALYSIS OF BRAIN ACTIVITY ENERGY EMISSION

BACKGROUND

1. Field

The disclosure of the present patent application relates to a device for measuring energy from the brain activity of students, thereby permitting the classification of students with certain learning disabilities based on the quantity of emitted energy.

2. Description of the Related Art

There is a current need to enhance the effectiveness of the educational system and reduce expenses associated with providing study programs unsuitable for students with intellectual learning difficulties. This objective entails classifying students based on the severity of their intellectual learning difficulties (mild, moderate, severe), grouping them into specialized classes, and delivering tailored educational programs. These efforts aim to foster economic development and facilitate the attainment of sustainable development for society. However, it is currently difficult to quantify the severity of a student's intellectual learning difficulties and classify students as a result.

Measuring brain energy speed and quantity is grounded in the nature of electrochemical energy transmitted between nerve cells within the brain. This electrochemical energy is a consequence of chemical reactions in the brain that facilitate the transmission of electrical charges between nerve cells in the form of currents. Waves of electrical charges travel between these nerve cells, executing their designated functions. The quantity and speed of these electrical charge transmissions escalate due to chemical reactions induced by the secretion of hormones in the body.

The electrochemical energy produced within the brain encompasses a magnetic field with effects extending beyond the skull. Utilizing external electronic sensors installable on the head, this magnetic field of electrochemical energy in the brain can be detected, and its intensity accurately measured.

Thus, a device and method for quantifying the severity of a student's intellectual learning difficulties and classifying students accordingly solving the aforementioned problems is desired.

SUMMARY

The present subject matter relates to the finding that, based on genetic analysis of students with learning difficulties, it is feasible to identify the specific gene accountable for neurological defects in the brain, thereby causing learning difficulties. This knowledge can enable interventions aimed at addressing learning difficulties at the embryonic stage during the formative period before birth, utilizing appropriate genetic analyses. Certain variables, such as consanguineous marriage and the analysis of mental abilities in prospective couples, can be utilized to make predictions about the likelihood of learning difficulties in fetuses.

Accordingly, in an embodiment, the present subject matter relates to an electronic device that detects and analyzes the energy emitted by brains of individuals. This device measures and analyzes the energy emitted from the brain activity of, for example, students, enabling the classification of students with learning difficulties based on the quantity of emitted energy. The concept behind this device bears resemblance to various technologies, such as the device used to record the thoughts of physicist Stephen William Hawking, iris diagnostic recognition devices, and lie detectors. Leveraging established measuring devices, supported by computer programs akin to those utilized in electrocardiography, enables the prediction of both the quantity and speed of brain energy based on the magnetic field's intensity. By comparing the intensity of the magnetic field resulting from electrochemical energy in the brain with standard measurements for the general populace, learning difficulties can be diagnosed effectively.

In another embodiment, students are exposed to a specific component of a device designed to detect and analyze energy emitted by brain activity of the student as they engage with a simple problem that they are working on solving. The presented problems span a range of difficulty levels, from easy to challenging. After each session, the emitted energy from the mental activity can be measured and analyzed. Subsequently, the extent of the student's learning difficulty can be identified and classified into one of three categories: mild, moderate, or severe, based on the analysis of their mental energy.

In an additional embodiment, the present subject matter can minimize educational setbacks arising from enrolling students with intellectual learning difficulties in programs designed for average students. By transitioning such students to programs that align with their mental abilities, their educational loss is reduced. This approach ensures that students with intellectual learning difficulties receive appropriate educational opportunities, enabling them to thrive and reach their full potential.

In a further embodiment, the present subject matter relates to the use of artificial intelligence (AI) technology and sophisticated computer programs in the present systems, methods, and devices. When used, such AI activity can enhance the effectiveness and efficiency of the present systems, methods, and devices, allowing for more accurate measurements and analysis of emitted energy. As such, artificial intelligence and advanced computer programs can potentially lead to improved outcomes and greater potential for application in various educational contexts.

In one embodiment, the present subject matter relates to an electronic device for detecting and analyzing energy emitted by a brain of an individual, the electronic device comprising: one or more sensors configured to be attached to a head of the individual to detect and measure electrical energy emitted by the brain of the individual; a brain-computer interface configured to receive electrical energy measured by the one or more sensors, analyze the electrical energy based on its quantity and speed, categorize the individual into one of three pre-programmed levels of learning difficulty, and translate the electrical energy into light waves; and a screen for displaying the light waves as a color spectrum.

In another embodiment, the present subject matter relates to an electronic device for detecting and analyzing energy emitted by a brain of an individual, the electronic device comprising: one or more sensors configured to wirelessly detect and measure electrical energy emitted by the brain of the individual; a brain-computer interface configured to receive electrical energy measured by the one or more sensors, analyze the electrical energy based on its quantity and speed, categorize the individual into one of three pre-programmed levels of learning difficulty, and translate the electrical energy into light waves; and a screen for displaying the light waves as a color spectrum.

These and other features of the present subject matter will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1A:
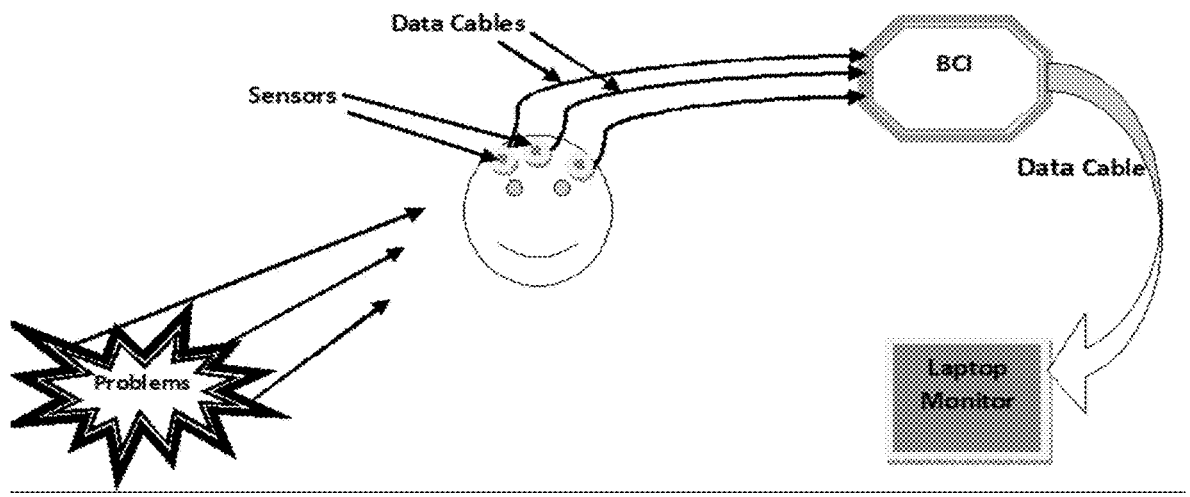
FIGS. 1A-1B are schematic diagram of embodiments of the present proposed device, with FIG. 1A being a wired embodiment and FIG. 1B being a wireless embodiment.

The following definitions are provided for the purpose of understanding the present subject matter and for construing the appended patent claims.

Definitions

It should be understood that the drawings described above or below are for illustration purposes only. The drawings are not necessarily to scale, with emphasis generally being placed upon illustrating the principles of the present teachings. The drawings are not intended to limit the scope of the present teachings in any way.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" or "individual" as used herein refers to a subject in need of treatment of a condition, disorder, or disease, such as a learning difficulty.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to the finding that, based on genetic analysis of students with learning difficulties, it is feasible to identify the specific gene accountable for neurological defects in the brain, thereby causing learning difficulties. This knowledge can enable interventions aimed at addressing learning difficulties at the embryonic stage during the formative period before birth, utilizing appropriate genetic analyses. Certain variables, such as consanguineous marriage and the analysis of mental abilities in prospective couples, can be utilized to make predictions about the likelihood of learning difficulties in fetuses.

Accordingly, in an embodiment, the present subject matter relates to an electronic device that detects and analyzes the energy emitted by brains of individuals. This device measures and analyzes the energy emitted from the brain activity of, for example, students, enabling the classification of students with learning difficulties based on the quantity of emitted energy. The concept behind this device bears resemblance to various technologies, such as the device used to record the thoughts of physicist Stephen William Hawking, iris diagnostic recognition devices, and lie detectors.

In another embodiment, students are exposed to a specific component of a device designed to detect and analyze energy emitted by brain activity of the student as they engage with a simple problem that they are working on solving. The presented problems span a range of difficulty levels, from easy to challenging. After each session, the emitted energy from the mental activity can be measured and analyzed. Subsequently, the extent of the student's learning difficulty can be identified and classified into one of three categories: mild, moderate, or severe, based on the analysis of their mental energy.

In an additional embodiment, the present subject matter can minimize educational setbacks arising from enrolling students with intellectual learning difficulties in programs designed for average students. By transitioning such students to programs that align with their mental abilities, their educational loss is reduced. This approach ensures that students with intellectual learning difficulties receive appropriate educational opportunities, enabling them to thrive and reach their full potential.

In a further embodiment, the present subject matter relates to the use of artificial intelligence (AI) technology and sophisticated computer programs in the present systems, methods, and devices. When used, such AI activity can enhance the effectiveness and efficiency of the present systems, methods, and devices, allowing for more accurate measurements and analysis of emitted energy. As such, artificial intelligence and advanced computer programs can potentially lead to improved outcomes and greater potential for application in various educational contexts.

The present electronic devices and systems revolve around the reception of electrical energy emanating from the human brain during contemplation of solutions to life situations and diverse challenges. Subsequently, this energy can be quantified in terms of quantity and velocity before being transmuted into a color spectrum or numerical data utilizing a Brain-Computer Interface (BCI) device. The resulting color spectrum or numerical representation is then displayed on a computer screen, where it can be subject to interpretation contingent upon the complexity of the brain's activity.

Accordingly, in one embodiment, the present subject matter relates to an electronic device for detecting and analyzing energy emitted by a brain of an individual, the electronic device comprising: one or more sensors configured to be attached to a head of the individual to detect and measure electrical energy emitted by the brain of the individual; a brain-computer interface configured to receive electrical energy measured by the one or more sensors, analyze the electrical energy based on its quantity and speed, categorize the individual into one of three pre-programmed levels of learning difficulty, and translate the electrical energy into light waves; and a screen for displaying the light waves as a color spectrum.

In an embodiment in this regard, the electrical energy emitted by the brain of the individual can originate from electrical output of the brain of the individual during a cognitive process. In this regard, the cognitive process can occur when the individual is presented with a scientific query or a research problem to contemplate for potential solutions.

In an additional embodiment, among the light waves displayed on the screen, green light waves signify a pre-programmed level of minimal learning difficulty, yellow light waves signify a pre-programmed level of moderate difficulty, and red light waves signify a pre-programmed level of substantial difficulty. In this regard, the brain-computer interface can further translate the color spectrum into numerical values, with values of 1-10 signifying the pre-programmed level of minimal learning difficulty, values of 11-20 signifying the pre-programmed level of moderate difficulty, and values of 21-30 signifying the pre-programmed level of substantial difficulty.

In an additional embodiment, the pre-programmed level of minimal learning difficulty, the pre-programmed level of moderate difficulty, and the pre-programmed level of substantial difficulty can be derived from previous measurements taken from students previously diagnosed with weak, moderate, or sever levels of learning difficulties. In this regard, the previous measurements can be related to quantity and speed of electrical energy emitted from the students previously diagnosed during their cognitive processes.

In a further embodiment, the brain-computer interface can further identify any genetic markers in the individual responsible for neurological defects in the individual's brain leading to one or more of the learning difficulties.

In another embodiment, the present subject matter relates to an electronic device for detecting and analyzing energy emitted by a brain of an individual, the electronic device comprising: one or more sensors configured to wirelessly detect and measure electrical energy emitted by the brain of the individual; a brain-computer interface configured to receive electrical energy measured by the one or more sensors, analyze the electrical energy based on its quantity and speed, categorize the individual into one of three pre-programmed levels of learning difficulty, and translate the electrical energy into light waves; and a screen for displaying the light waves as a color spectrum.

Figure 1B:
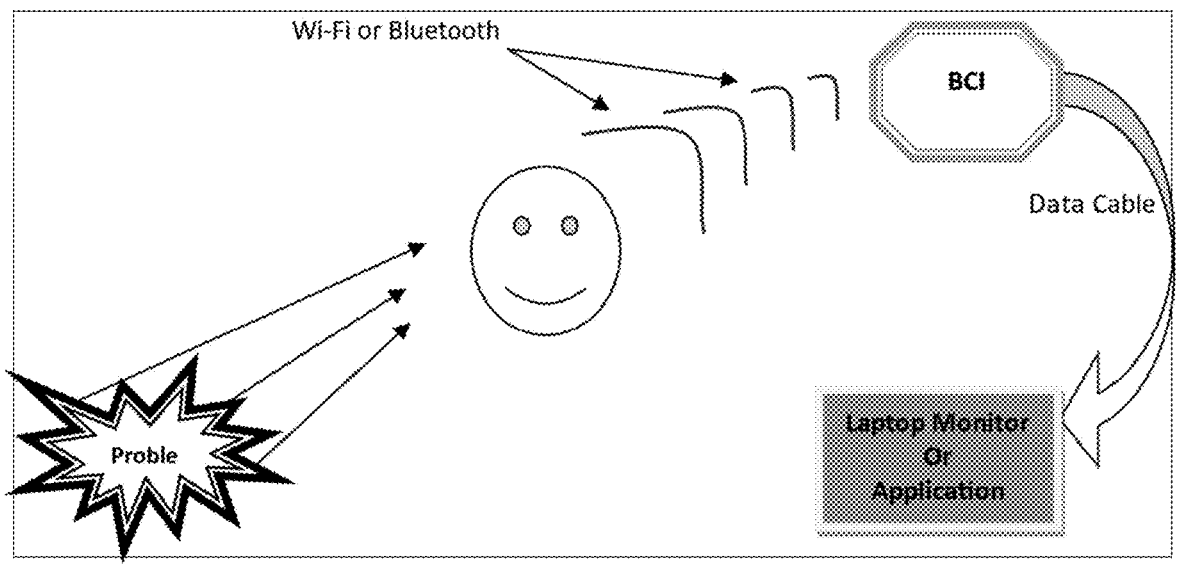

Referring to the schematic of FIG. 1A, the utilized sensors included with the present device share similarities with those commonly found in both the Brain-Computer Interface (BCI) device and lie detectors. These sensors can establish contact with various regions of the head, facilitating the detection of electrical energy. In certain embodiments, as shown in FIG. 1B, the sensors can be wirelessly connected to the rest of the device. In other embodiments, the sensors can be connected to the rest of the device by, e.g., data cables as shown in FIG. 1A. In other embodiments, the sensors can be remote sensors that are not physically attached to the individual's head, but which can harness the capabilities of artificial intelligence technology and advanced computer programs to remotely detect and capture the human-generated energy as per FIG. 1B. Subsequently, the sensors can operate with the rest of the device to analyze this data and categorize students based on their individual conditions and levels of difficulty.

The wireless embodiment of FIG. 1B can offer significant advantages by circumventing the challenges associated with sensors that are in close proximity to the human body and alleviating the psychological burden arising from such proximity. Accordingly, this embodiment can primarily rely on remote sensing sensors, aligning with established systems such as iris fingerprint and voice fingerprint technologies. Notably, this can facilitate student assessments within their natural states during the diagnostic phase, eliminating the influence of psychological pressure stemming from the attachment of sensors to the body. This non-invasive approach can ensure that students remain unhindered and at ease throughout the diagnostic process.

Next, the measured energy originates from the electrical output of students' brain activity during their cognitive processes. This occurs when students are presented with a scientific query or a research problem to contemplate for potential solutions.

The present device operates by receiving the electrical energy emanating from the brain during cognitive processes. This energy is subsequently analyzed based on its quantity and speed, allowing for the categorization of students into three fundamental levels of learning difficulty. Students are tasked with contemplating the resolution of problems spanning a range from easy to challenging.

Using the present device, the electrical energy emitted by the brain is quantified, assessed, and translated into light waves, manifesting as a color spectrum displayed on a television screen. This color spectrum is indicative of the degree of difficulty students encounter when solving problems, with green denoting minimal or weak difficulty, yellow signifying moderate difficulty, and red indicating substantial difficulty. Alternatively, the color spectrum can be translated into numerical values, such as 1-10 for low difficulty, 11-20 for moderate difficulty, and 21-30 for significant difficulty. The present device undergoes prior programming and is furnished with data derived from earlier measurements taken from students previously diagnosed with varying levels of learning difficulties, namely weak, moderate, or severe. These measurements pertain to the quantity and speed of electrical energy emitted during their cognitive processes.

The present device's programming can align with three distinct learning difficulty models. Consequently, the device can assess any student by analyzing the quantity and speed of electrical energy released during their problem-solving contemplation. Students can be classified based on the data programmed into the device. Furthermore, the device's programming can be adaptable and amenable to updates, catering to diverse educational environments and the varying developmental stages of students.

In more advanced stages of device development, and leveraging genetic analysis of individuals contemplating marriage, the potential exists to identify the genetic markers responsible for neurological defects in the brain that lead to cases of learning difficulties. This could pave the way for the early intervention and treatment of learning difficulties in fetal development during the embryonic stage, prior to birth, employing suitable genetic therapeutic approaches. Certain variables, including consanguineous marriages and the professional and academic backgrounds of individuals, can be utilized to formulate predictions regarding the likelihood of learning difficulties in fetuses.

It is to be understood that the device is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. An electronic device for detecting and analyzing energy emitted by a brain of an individual, the electronic device comprising:
   one or more sensors configured to be attached to a head of the individual to detect and measure electrical energy emitted by the brain of the individual;
   a brain-computer interface configured to receive electrical energy measured by the one or more sensors, analyze the electrical energy based on its quantity and speed, categorize the individual into one of three pre-programmed levels of learning difficulty, and convert the electrical energy into light waves; and
   a screen for displaying the light waves as a color spectrum.

2. The electronic device for detecting and analyzing energy emitted by a brain of an individual of claim 1, wherein the electrical energy emitted by the brain of the individual originates from electrical output of the brain of the individual during a cognitive process.

3. The electronic device for detecting and analyzing energy emitted by a brain of an individual of claim 2, wherein the cognitive process occurs when the individual is presented with a scientific query or a research problem to contemplate for potential solutions.

4. The electronic device for detecting and analyzing energy emitted by a brain of an individual of claim 2, wherein, among the light waves displayed on the screen, green light waves signify a pre-programmed level of minimal learning difficulty, yellow light waves signify a pre-programmed level of moderate difficulty, and red light waves signify a pre-programmed level of substantial difficulty.

5. The electronic device for detecting and analyzing energy emitted by a brain of an individual of claim 4, wherein the brain-computer interface further translates the color spectrum into numerical values, with values of 1-10 signifying the pre-programmed level of minimal learning difficulty, values of 11-20 signifying the pre-programmed level of moderate difficulty, and values of 21-30 signifying the pre-programmed level of substantial difficulty.

6. The electronic device for detecting and analyzing energy emitted by a brain of an individual of claim 4, wherein the pre-programmed level of minimal learning difficulty, the pre-programmed level of moderate difficulty, and the pre-programmed level of substantial difficulty are derived from previous measurements taken from students previously diagnosed with weak, moderate, or severe levels of learning difficulties.

7. The electronic device for detecting and analyzing energy emitted by a brain of an individual of claim 6, wherein the previous measurements are related to quantity and speed of electrical energy emitted from the students previously diagnosed during their cognitive processes.

8. The electronic device for detecting and analyzing energy emitted by a brain of an individual of claim 1, wherein the brain-computer interface further identifies any genetic markers in the individual responsible for neurological defects in the individual's brain leading to one or more of the learning difficulties.

9. The electronic device for detecting and analyzing energy emitted by a brain of an individual of claim 1, wherein the one or more sensors are remote sensors that harness artificial intelligence and advanced computer programs to remotely detect and capture the electrical energy.

10. An electronic device for detecting and analyzing energy emitted by a brain of an individual, the electronic device comprising:
    one or more sensors configured to wirelessly detect and measure electrical energy emitted by the brain of the individual;
    a brain-computer interface configured to receive electrical energy measured by the one or more sensors, analyze the electrical energy based on its quantity and speed, categorize the individual into one of three pre-programmed levels of learning difficulty, and convert the electrical energy into light waves; and a screen for displaying the light waves as a color spectrum.

\* \* \* \* \*